(12) United States Patent
Obara et al.

(10) Patent No.: US 11,711,615 B2
(45) Date of Patent: Jul. 25, 2023

(54) WORKPIECE INSPECTION DEVICE AND WORKPIECE INSPECTION METHOD

(71) Applicant: HONDA MOTOR CO., LTD., Tokyo (JP)

(72) Inventors: Ryo Obara, Tochigi (JP); Masaki Isokawa, Tochigi (JP); Yasuhisa Saito, Tochigi (JP); Manabu Yamamoto, Tochigi (JP); Masashi Machida, Tochigi (JP); Jun Shiwaku, Tochigi (JP)

(73) Assignee: HONDA MOTOR CO., LTD., Tokyo (JP)

(*) Notice: Subject to any disclaimer, the term of this patent is extended or adjusted under 35 U.S.C. 154(b) by 0 days.

(21) Appl. No.: 17/311,496

(22) PCT Filed: Nov. 22, 2019

(86) PCT No.: PCT/JP2019/045794
§ 371 (c)(1),
(2) Date: Jun. 7, 2021

(87) PCT Pub. No.: WO2020/121784
PCT Pub. Date: Jun. 18, 2020

(65) Prior Publication Data
US 2022/0021813 A1    Jan. 20, 2022

(30) Foreign Application Priority Data

Dec. 11, 2018   (JP) ................................. 2018-231674

(51) Int. Cl.
*H04N 23/695*   (2023.01)
*G01N 21/88*    (2006.01)
(Continued)

(52) U.S. Cl.
CPC ....... *H04N 23/695* (2023.01); *G01N 21/8851* (2013.01); *G06T 7/0004* (2013.01);
(Continued)

(58) Field of Classification Search
CPC ....... G01N 21/8851; G01N 2021/8867; G01N 2021/887; G06T 7/0004; G06T 7/0006;
(Continued)

(56) References Cited

U.S. PATENT DOCUMENTS

| 11,442,445 B2* | 9/2022 | Cella ........................ G06N 3/02 |
| 2009/0245614 A1* | 10/2009 | Baldwin ............ G01N 21/8806 382/141 |

(Continued)

FOREIGN PATENT DOCUMENTS

| JP | H01-155248 | 6/1989 |
| JP | H06330810 A * | 11/1994 |

(Continued)

OTHER PUBLICATIONS

Z. Fei, J. Guo, J. Wang and G. Luo, "The application of laser and CCD compound measuring method on 3D object detection," 2010 IEEE International Conference on Mechatronics and Automation, 2010, pp. 1199-1202, doi: 10.1109/ICMA.2010.5588049 (Year: 2010).*

(Continued)

*Primary Examiner* — Michael Robert Cammarata
(74) *Attorney, Agent, or Firm* — Rankin, Hill & Clark LLP (57) ABSTRACT

A workpiece inspection device 1 includes a table (3), image capturing unit fixing part (7), first light projection unit (4), second light projection unit (5), linear movement mechanism (8), turning mechanism (9), quality determination unit (10), and control unit (11). The control unit (11) performs first image capturing step of causing first light projection
(Continued)

unit (4) to project light and causing image capturing unit (6) to capture image, detailed inspection portion-determination step of setting, portion of workpiece (2) determined to require detailed inspection based on image captured in the first image capturing step, second image capturing step of causing second light projection unit (5) to project light onto the workpiece (2) and causing image capturing unit (6) to capture image of the detailed inspection-requiring portion, and quality determination step of determining quality of the detailed inspection-requiring portion based on image captured in the second image capturing step.

8 Claims, 8 Drawing Sheets

(51) Int. Cl.
    *G06T 7/00*     (2017.01)
    *H04N 23/56*     (2023.01)
    *G01N 33/00*     (2006.01)

(52) U.S. Cl.
    CPC ..... *H04N 23/56* (2023.01); *G01N 2021/8887* (2013.01); *G01N 2033/0078* (2013.01); *G06T 2207/10152* (2013.01); *G06T 2207/30164* (2013.01)

(58) Field of Classification Search
    CPC ........ G06T 7/0008; G06T 2207/10152; H04N 5/2256
    See application file for complete search history.

(56) References Cited

U.S. PATENT DOCUMENTS

| | | | | |
|---|---|---|---|---|
| 2011/0103679 | A1* | 5/2011 | Campbell | G02B 7/36 |
| | | | | 382/152 |
| 2017/0270651 | A1* | 9/2017 | Bailey | G06T 7/001 |
| 2018/0106607 | A1* | 4/2018 | Umemura | G06F 17/11 |
| 2019/0120770 | A1* | 4/2019 | Chen | G06T 7/001 |
| 2019/0381736 | A1* | 12/2019 | Jensen | B29C 64/393 |
| 2022/0281612 | A1* | 9/2022 | Inaoka | H02J 7/1415 |

FOREIGN PATENT DOCUMENTS

| | | | | |
|---|---|---|---|---|
| JP | H0723210 U | * | 4/1995 | |
| JP | 2002-005850 | | 1/2002 | |
| JP | 2009-128325 | | 6/2009 | |
| JP | 2009-162563 | | 7/2009 | |
| JP | 2009216453 A | * | 9/2009 | ......... G01N 21/954 |
| JP | 2011-141135 | | 7/2011 | |
| JP | 2013242256 A | * | 12/2013 | |
| JP | 2013242257 A | * | 12/2013 | |
| JP | 2014-109530 | | 6/2014 | |
| JP | 2014235066 A | * | 12/2014 | |
| JP | 2018-194443 | | 12/2018 | |
| JP | 2020008390 A | * | 1/2020 | |
| KR | 20160034049 A | * | 3/2016 | |
| WO | 00/25352 | | 5/2000 | |

OTHER PUBLICATIONS

Z. Zhang, Z. Chen, J. Shi, F. Jia and M. Dai, "Surface Roughness Vision Measurement in Different Ambient Light Conditions," 2008 15th International Conference on Mechatronics and Machine Vision in Practice, 2008, pp. 1-4, doi: 10.1109/MMVIP.2008.4749497 (Year: 2008).*

Wang X, Xie Z, Wang K, Zhou L. Research on a Handheld 3D Laser Scanning System for Measuring Large-Sized Objects. Sensors (Basel). Oct. 21, 2018;18(10):3567. doi: 10.3390/S18103567. PMID: 30347880; PMCID: PMC6210098. (Year: 2018).*

Shiyi Gao, Mingyang Zhao, Lei Zhang and Yuanyuan Zou, "Dual-beam structured light vision system for 3D coordinates measurement," 2008 7th World Congress on Intelligent Control and Automation, 2008, pp. 3687-3691, doi: 10.1109/WCICA.2008.4593515 (Year: 2008).*

Li, Xing-Qiang, Zhong Wang, and Lu-Hua Fu. "A laser-based measuring system for online quality control of car engine block." Sensors 16.11 (2016): 1877. (Year: 2016).*

International Search Report, dated Jan. 21, 2020, 2 pages.

* cited by examiner

WORKPIECE INSPECTION DEVICE AND WORKPIECE INSPECTION METHOD

TECHNICAL FIELD

The present invention relates to a workpiece inspection device and a workpiece inspection method.

BACKGROUND ART

There has conventionally been known an inspection device that determines the quality of a glass substrate based on image data obtained by capturing an image of the glass substrate (for example, see Japanese Patent Laid-Open No. 2002-5850).

CITATION LIST

Patent Literature

Patent Literature 1: Japanese Patent Laid-Open No. 2002-5850

SUMMARY OF INVENTION

Technical Problem

As a device that inspects a workpiece based on an image obtained by capturing an image of the workpiece, an inspection device that determines the quality of the workpiece by planar image analysis based on the captured image, height difference analysis based on an image using slit light, or the like may be used. However, in general, there is a problem in which a cycle time of inspection is increased when inspection accuracy is improved.

In view of the above circumstances, an object of the present invention is to provide a workpiece inspection device capable of performing an inspection with high accuracy and reducing a cycle time of the inspection, and a workpiece inspection method.

Solution to Problem

[1] In order to achieve the above-described object, the present invention provides a workpiece inspection device configured to capture an image of a surface of a workpiece by an image capturing unit and determine quality of the workpiece, the workpiece inspection device comprising:

a table on which the workpiece is placed;

an image capturing unit fixing part configured to fix the image capturing unit disposed at a position spaced apart from the workpiece;

a first light projection unit;

a second light projection unit;

a linear movement mechanism configured to linearly move the table or the image capturing unit fixing part to freely adjust a relative distance between the table and the image capturing unit fixing pail;

a turning mechanism that has a rotation axis extending in a direction perpendicular to a moving direction of the linear movement mechanism, configured to freely turn the image capturing unit with respect to the image capturing unit fixing part around the rotation axis;

a quality determination unit configured to determine the quality of the workpiece based on the image captured by the image capturing unit; and a control unit configured to control the linear movement mechanism and the turning mechanism, wherein the control unit performs:

a first image capturing step of causing the first light projection unit to project light onto the workpiece and causing the image capturing unit to capture an image;

a detailed inspection portion-determination step of setting, as a detailed inspection-requiring portion, a portion of the workpiece that is determined to require a detailed inspection based on the image captured in the first image capturing step, when present;

a second image capturing step of causing the second light projection unit to project light onto the workpiece and causing the image capturing unit to capture an image of the detailed inspection-requiring portion in a case where the detailed inspection-requiring portion is set in the detailed inspection portion-determination step; and a quality determination step of determining the quality of the detailed inspection-requiring portion based on the image captured in the second image capturing step.

According to the present invention, an image of only a portion that is determined to require a detailed inspection when an image is captured using the first light projection unit is captured using the second light projection unit to determine the quality of a final workpiece. Accordingly, there can be provided a workpiece inspection device that is capable of performing an inspection with high accuracy and reducing a cycle time of the inspection.

[2] In addition, in the present invention, it is preferable that the image capturing unit is movable by the turning mechanism to a first position where reflection light that is the light projected by the first light projection unit is specularly reflected from the workpiece is received, and is movable by the turning mechanism to a second position where reflection light that is the light projected at the workpiece by the second light projection unit at an incidence angle which is different from the incidence angle of the light projected at the workpiece by the first light projection unit is specularly reflected from the workpiece is received, and the linear movement mechanism adjusts a relative distance between the table and the image capturing unit fixing part so that a focus is adjusted to prevent focus deviation caused by a difference due to a difference in the incidence angle between when the reflection light of the light from the first light projection unit is received and when the reflection light of the light from the second light projection unit is received.

According to the present invention, even when images formed by the first light projection unit and the second light projection unit that project the light at different incidence angles, respectively, are captured by a single image capturing unit, it is possible to adjust the focus of the image capturing unit by adjusting the relative distance between the table and the image capturing unit fixing part using the linear movement mechanism.

[3] In addition, in the present invention, it is preferable that the table is provided with a moving mechanism configured to move the workpiece, and the image capturing unit fixing part is disposed at an interval from the table to reduce or prevent transmission of vibrations from the moving mechanism.

According to the present invention, the vibrations from the moving mechanism can be less likely to be transmitted to the image capturing unit and the inspection can be performed with high accuracy, even when inspecting the workpiece while moving the workpiece at a relatively high speed using the moving mechanism.

[4] In addition, in the present invention, it is preferable that the first light projection unit is for measuring a two-dimensional shape, the second light projection unit is for measuring a three-dimensional shape, the image capturing unit comprises an image capturing element, when the two-dimensional shape is measured using the first light projection unit, the detailed inspection-requiring portion is set based on image data detected by the image capturing element, and when the three-dimensional shape is measured using the second light projection unit, the quality of the workpiece is determined based on image data detected by the image capturing element.

According to the present invention, an image of only a portion that is determined to require a detailed inspection when an image is captured using the first light projection unit is captured using the second light projection unit to determine the quality of a final workpiece. Accordingly, there can be provided a workpiece inspection device that is capable of performing an inspection with high accuracy and reducing a cycle time of the inspection.

[5] In addition, in the present invention, it is preferable that the workpiece is a cylinder block of an internal combustion engine, and the table is comprises a fixing mechanism configured to fix the cylinder block to the table in a state where the cylinder block is placed on the table with a face of the cylinder block to which a crankcase is to be attached facing the table so that a cylinder arrangement direction of the cylinder block corresponds to a horizontal direction.

According to the present invention, an image of only a portion that is determined to require a detailed inspection when an image is captured using the first light projection unit is captured using the second light projection unit to determine the quality of a final cylinder block. Accordingly, there can be provided a workpiece inspection device that is capable of performing an inspection with high accuracy and reducing a cycle time of the inspection.

[6] A workpiece inspection method of the present invention comprises:

a first image capturing step of projecting light onto a workpiece by a first light projection unit and capturing an image of the workpiece by an image capturing unit;

a first quality determination step of determining the quality of the workpiece based on the image captured in the first image capturing step;

a second image capturing step of projecting slit light onto the workpiece by a second light projection unit and capturing, by the image capturing unit, an image of a first defect-determined portion which is a portion of the workpiece determined to be defective in the first quality determination step; and a second quality determination step of detecting unevenness on a surface of the workpiece from a shape of an edge of the slit light to determine the quality of the first defect-determined portion based on the image captured in the second image capturing step.

According to the workpiece inspection method of the present invention, an image of only a portion that is determined to require a detailed inspection when an image is captured using the first light projection unit is captured using the second light projection unit to determine the quality of a final workpiece. Accordingly, there can be provided a workpiece inspection method that is capable of performing an inspection with high accuracy and reducing a cycle time of the inspection.

DESCRIPTION OF EMBODIMENT

Figure 1:
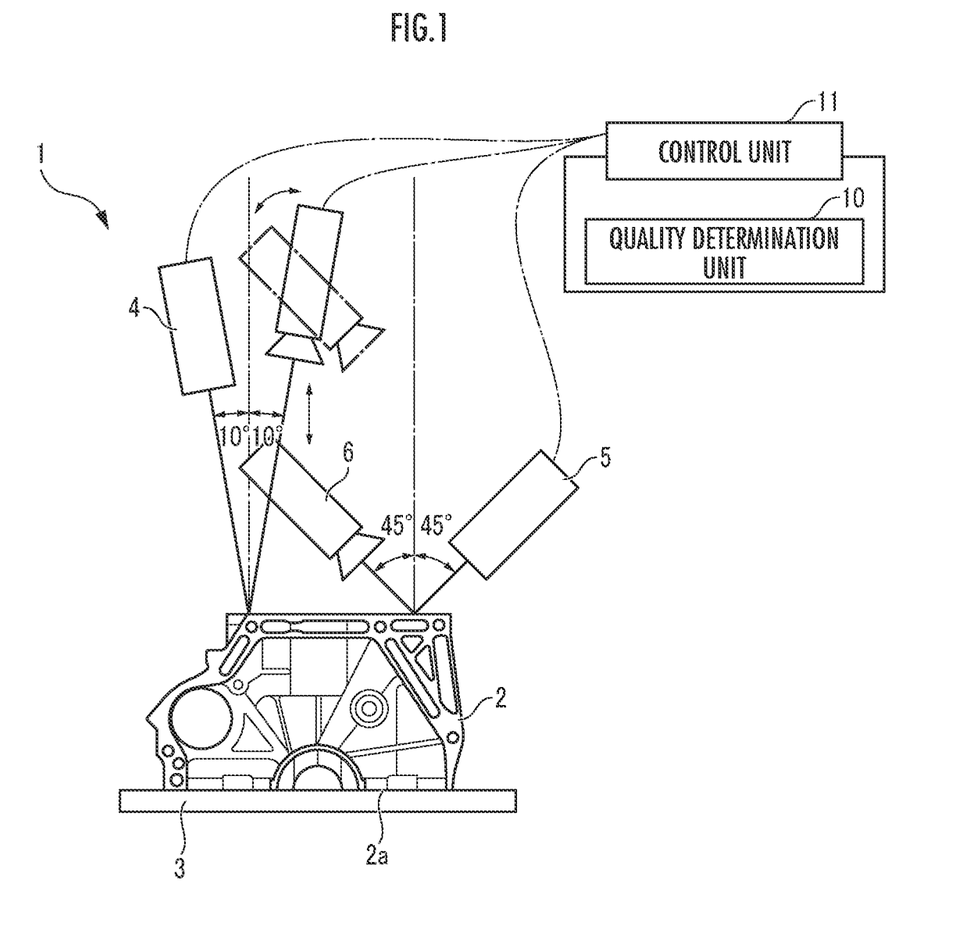
FIG. 1 is an explanatory diagram schematically illustrating an embodiment of a workpiece inspection device of the present invention.

An embodiment of a workpiece inspection device and a workpiece inspection method of the present invention will be described with reference to FIGS. 1 to 12. A workpiece inspection device 1 of the present embodiment comprises a table 3 on which a workpiece 2 is placed, a first light projection unit 4 that projects light onto an inspection target face of the workpiece 2, a second light projection unit 5 that projects slit light onto the inspection target face of the workpiece 2, and an image capturing unit 6 including a camera that captures an image of the inspection target face of the workpiece 2, as illustrated in FIG. 1, and an image capturing unit fixing par 7 by which the image capturing unit 6 is disposed at a position spaced apart from the inspection target face of the workpiece 2, a linear movement mechanism 8 configured to linearly move the image capturing unit fixing part 7 to freely adjust a relative distance between the table 3 and the image capturing unit fixing part 7, and a turning mechanism 9 that has a rotation axis 9a extending in a direction perpendicular to a moving direction of the linear movement mechanism 8, configured to freely turn the image capturing unit 6 with respect to the image capturing unit fixing part 7 around the rotation axis 9a, as illustrated in FIG. 4, and a quality determination unit 10 that determines the quality of the inspection target face of the workpiece 2 based on the image captured by the image capturing unit 6, and a control unit 11 configured to control the first light projection unit 4, the second light projection unit 5, the image capturing unit 6, the linear movement mechanism 8, and the turning mechanism 9, as illustrated in FIG. 1.

The quality determination unit 10 is a part of the control unit 11. The control unit 11 includes an electronic unit constituted by a CPU, a memory, and the like, and has a function of determining the quality of the inspection target face of the workpiece 2 based on the image captured by the image capturing unit 6, by executing, in the CPU, a control program held in a storage unit such as a memory.

The control unit 11 performs a first image capturing step of causing the first light projection unit 4 to project the light onto the inspection target face of the workpiece 2 and causing the image capturing unit 6 to capture an image of the inspection target face of the workpiece 2, a detailed inspection portion-determination step of setting, as a detailed inspection-requiring portion, a portion that is determined to require a detailed inspection in the inspection target face of the workpiece 2 based on the image captured in the first image capturing step, when present, a second image capturing step of causing the second light projection unit 5 to project the light onto the workpiece 2 and causing the image capturing unit 6 to capture an image of the portion in the inspection target face of the workpiece 2 that is selected as the detailed inspection-requiring portion in the detailed inspection portion-determination step, and a quality determination step of determining the quality of the detailed inspection-requiring portion based on the image captured in the second image capturing step.

Figure 2:
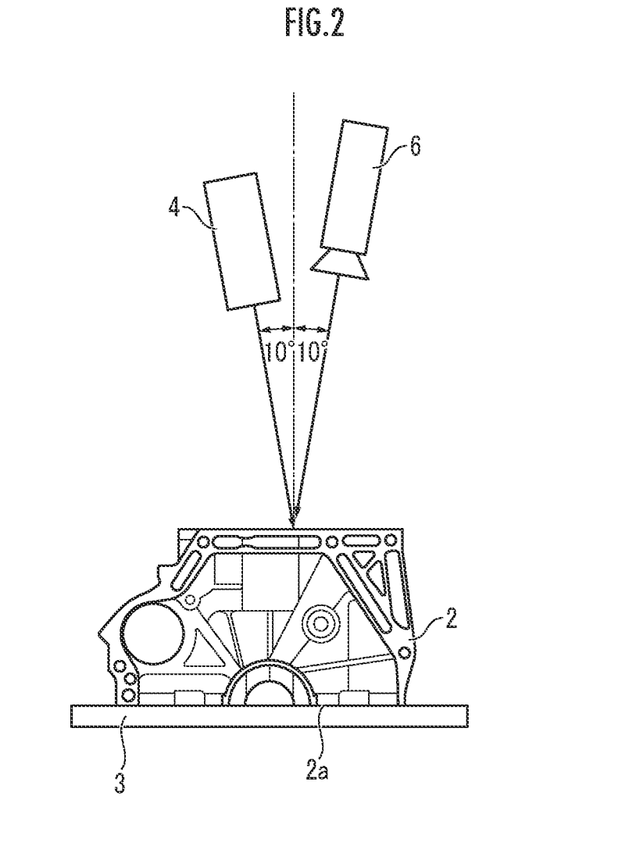
FIG. 2 is an explanatory diagram illustrating an inspection using a first light projection unit in the workpiece inspection device of the present embodiment.
Figure 3:
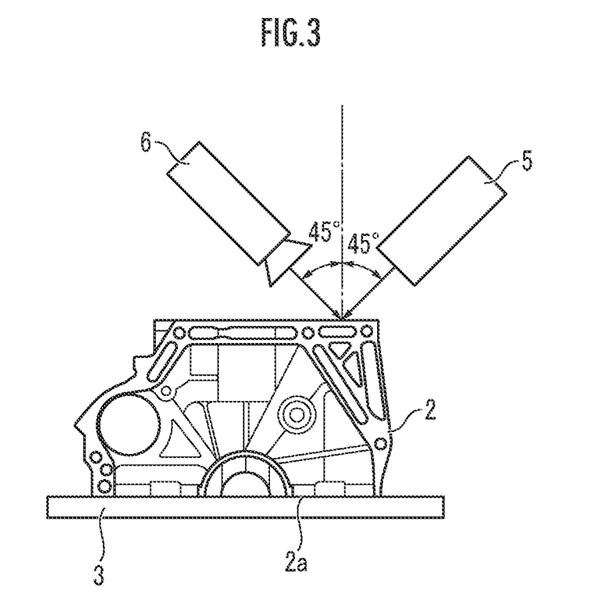
FIG. 3 is an explanatory diagram illustrating an inspection using a second light projection unit in the workpiece inspection device of the present embodiment.
Figure 4:
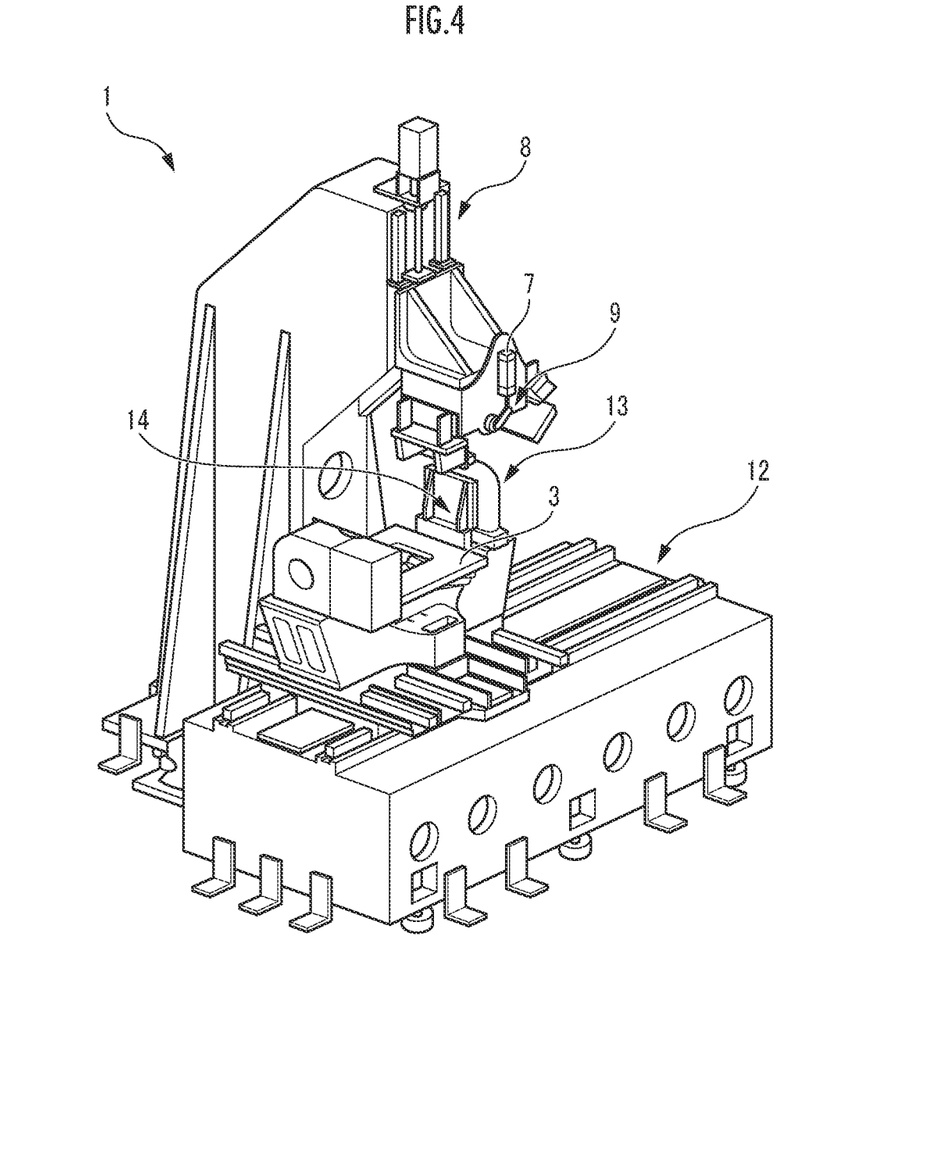
FIG. 4 is an explanatory diagram schematically illustrating the workpiece inspection device of the present embodiment.

The image capturing unit 6 is movable by the turning mechanism 9 and the linear movement mechanism 8 to a first position where reflection light that is the light projected by the first light projection unit 4 is specularly reflected from the inspection target face the workpiece 2 is received, as illustrated in FIG. 2, and is movable by the turning mechanism 9 and the linear movement mechanism 8 to a second position where reflection light that is the light projected at the inspection target face of the workpiece by the second light projection unit 5 at an incidence angle (for example, 45 degrees) which is different from the incidence angle (for example, 10 degrees) of the light projected at the inspection target face of the workpiece by the first light projection unit 4 is specularly reflected from the inspection target face of the workpiece is received, as illustrated in FIG. 3.

The control unit 11 causes the linear movement mechanism 8 to adjust the relative distance between the table 3 and the image capturing unit fixing part 7 so that a focus is adjusted to prevent focus deviation caused by a difference due to a difference in the incidence angle between when the reflection light of the light from the first light projection unit 4 is received and when the reflection light of the light from the second light projection unit 5 is received (in other words, so that a working distance (from the end of the lens to an object) is kept constant between when an image is captured using the first light projection unit 4 and when an image is captured using the second light projection unit 5). Note that FIG. 1 is a schematic diagram, and therefore does not illustrate that the working distance is kept constant therebetween. However, the working distance is actually set to be kept constant therebetween.

As illustrated in FIG. 4, the table 3 is provided with a moving mechanism 12 configured to move the workpiece 2 leftward, rightward, frontward and backward in the horizontal direction. In addition, the table 3 is also provided with a swing mechanism 13 configured to change the inspection target face among a back face, a top face, and a front face of the workpiece 2 while holding side faces of the workpiece 2.

The image capturing unit fixing part 7 is disposed at an interval from the table 3 to reduce or prevent the transmission of vibrations from the moving mechanism 12. Note that the term "at an interval" means that when the table 3 is disposed on a floor (ground) of a plant, the image capturing unit fixing part 7 may be also disposed on the floor (ground), but in this case, the table 3 and the image capturing unit fixing part 7 are disposed at an interval not to directly contact each other. The first light projection unit 4 is for measuring a two-dimensional shape, and the second light projection unit 5 is for measuring a three-dimensional shape. The image capturing unit 6 comprises an image capturing element.

When the two-dimensional shape is measured using the first light projection unit 4, the image capturing unit 6 determines whether the detailed inspection is required, based on the image data detected by the image capturing element of the image capturing unit 6. When the three-dimensional shape is measured using the second light projection unit 5, the image capturing unit 6 determines the quality of the detailed inspection-requiring portion based on the image data detected by the image capturing element of the image capturing unit 6. When it is determined that the detailed inspection-requiring portion is defective, the workpiece 2 is treated as a defective product.

The workpiece 2 is, for example, a cylinder block of an internal combustion engine. The table 3 is provided with a fixing mechanism 14 configured to fix the cylinder block serving as the workpiece 2 to the table 3 in a state where the cylinder block is placed on the table 3 with a face (one face 2a) of the cylinder block to which a crankcase is to be attached facing the table 3 so that a cylinder arrangement direction of the cylinder block corresponds to the horizontal direction.

In the inspection of a gasket face (a face on a cylinder head side) where high accuracy is required in the cylinder block, the cylinder block is disposed so that the measurement pixels in the two-dimensional measurement and the slit light in the three-dimensional measurement extend in a direction perpendicular to the cylinder arrangement direction, and is inspected, whereby machining (milling) scratches on the gasket face can be easily measured, and the machined surface of the workpiece 2 can be measured with high accuracy.

A workpiece inspection method of the present embodiment comprises a first image capturing step of projecting the light onto the workpiece 2 by the first light projection unit 4 and capturing an image of the workpiece 2 by the image capturing unit 6, a detailed inspection portion-determination step of setting, as a detailed inspection-requiring portion, a portion of the workpiece 2 that is determined to require a detailed inspection based on the image captured in the first image capturing step, when present, a second image capturing step of projecting the slit light onto the workpiece 2 by the second light projection unit 5 and capturing an image of the detailed inspection-requiring portion by the image capturing unit 6 in the case where the detailed inspection-requiring portion is set in the detailed inspection portion-determination step, and a quality determination step of detecting unevenness on the inspection target face (surface) of the workpiece 2 from a shape of an edge of the slit light to determine the quality of the detailed inspection-requiring portion based on the image captured in the second image capturing step.

Figure 5:
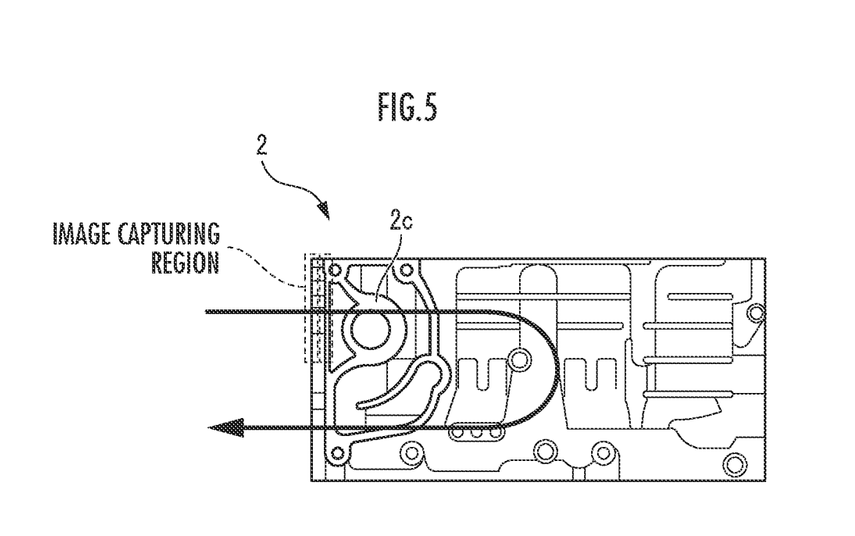
FIG. 5 is an explanatory diagram illustrating the order of image capturing of a first face of the workpiece by an arrow, in the workpiece inspection device of the present embodiment.
Figure 6:
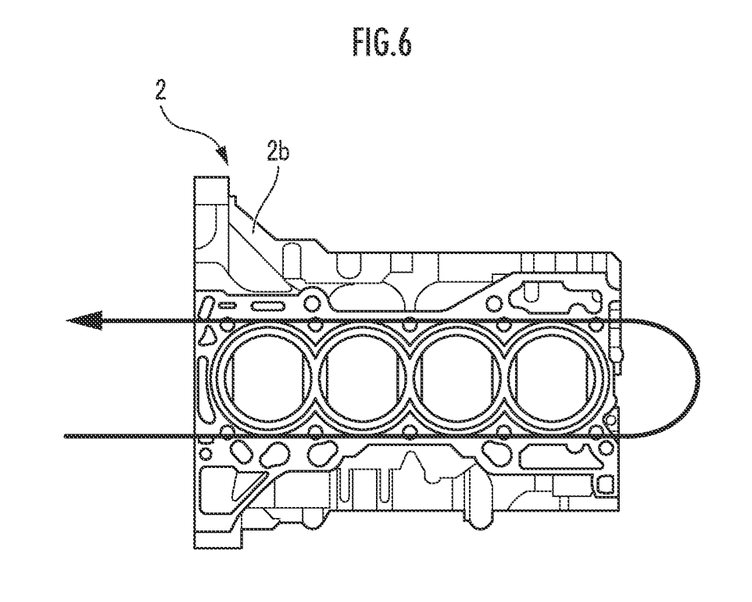
FIG. 6 is an explanatory diagram illustrating the order of image capturing of a second face (gasket face) of the workpiece by an arrow, in the workpiece inspection device of the present embodiment.
Figure 7:
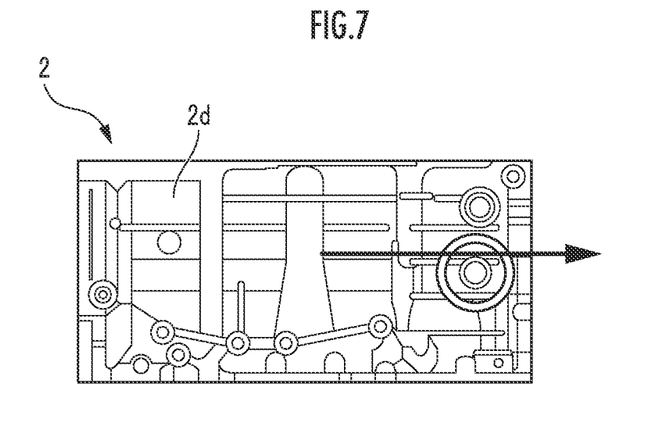
FIG. 7 is an explanatory diagram illustrating the order of image capturing of a third face of the workpiece by an arrow, in the workpiece inspection device of the present embodiment.

In the present embodiment, in the case where the cylinder block serving as the workpiece 2 is fixed to the table 3 in the state where a gasket face 2b (a face on a cylinder head side) faces upward, the swing mechanism 13 is used to swing the cylinder block, whereby the inspection can be performed not only on the gasket face 2b (the face on the cylinder head side: a second face) illustrated in FIG. 6 but also on a front face 2c (a first face) illustrated in FIG. 5 and a back face 2d (a third face) illustrated in FIG. 7.

Accordingly, in the workpiece inspection method using the workpiece inspection device 1 of the present embodiment, firstly, for each of faces shown in FIGS. 5 to 7 in order, the captured images sequentially captured along the arrows indicated in each figure with the light from the first light projection unit 4 are joined while partially overlapping each other, a difference from a pre-stored reference image with respect to the joined image is obtained to extract the luminance unevenness, and the difference image is subjected to the binarization processing to identify the detailed inspection-requiring portion.

Figure 8:
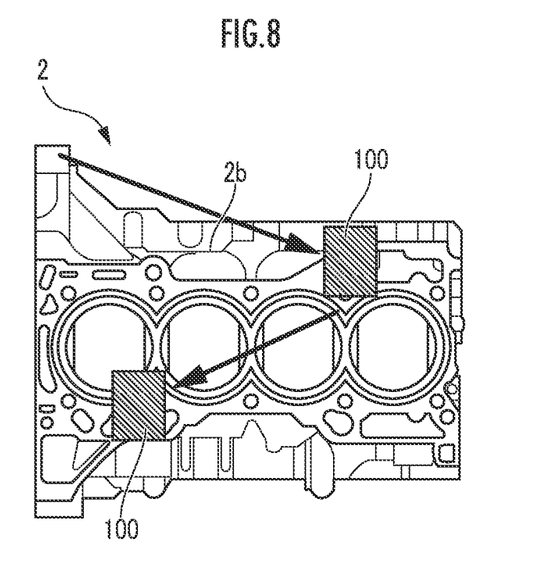
FIG. 8 is an explanatory diagram illustrating the order of image capturing of a detailed inspection in the second face (gasket face) of the workpiece by arrows, in the workpiece inspection device of the present embodiment.
Figure 9:
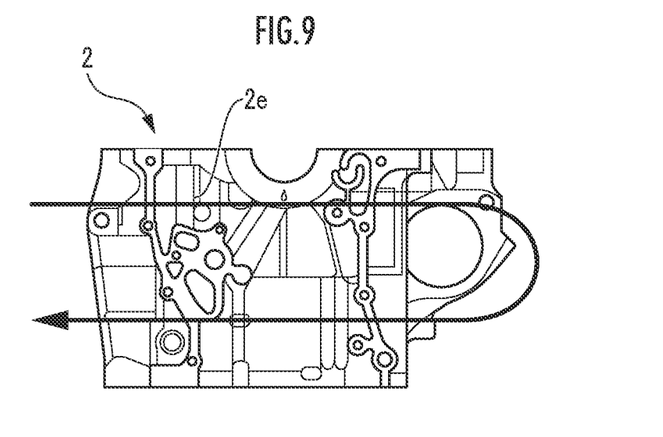
FIG. 9 is an explanatory diagram illustrating the order of image capturing of a fourth face of the workpiece by an arrow, in the workpiece inspection device of the present embodiment.
Figure 10:
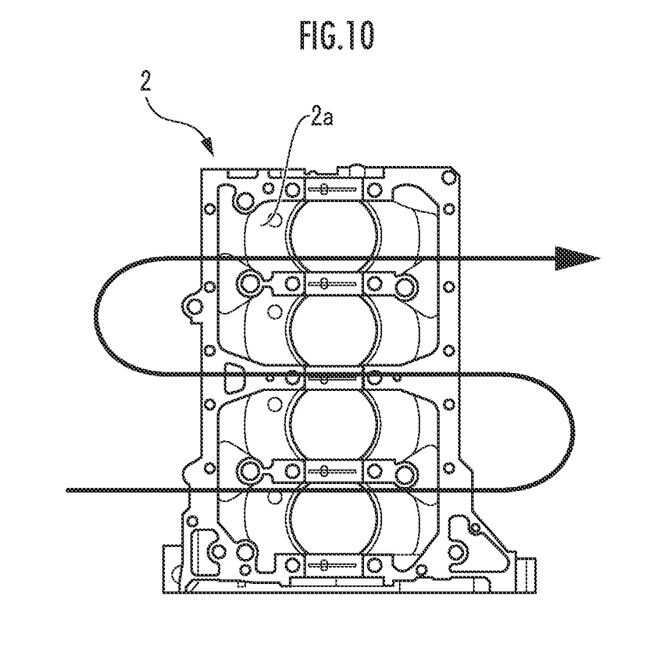
FIG. 10 is an explanatory diagram illustrating the order of image capturing of a fifth face (face on a crankshaft side) of the workpiece by an arrow, in the workpiece inspection device of the present embodiment.
Figure 11:
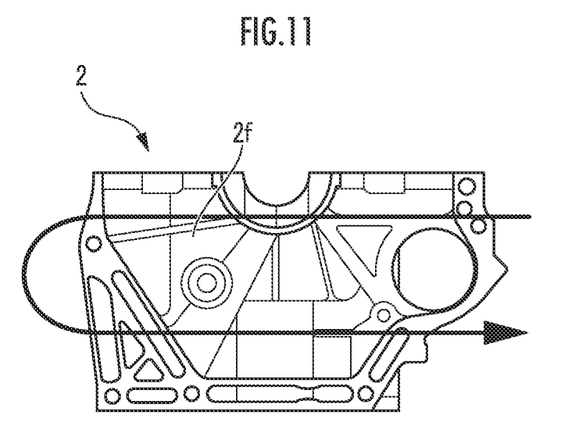
FIG. 11 is an explanatory diagram illustrating the order of image capturing of a sixth face of the workpiece by an arrow, in the workpiece inspection device of the present embodiment.

Next, in the case where two detailed inspection-requiring portions are identified on the gasket face 2b (the face on the cylinder head side: the second face) as illustrated in FIG. 8, the positions of the detailed inspection-requiring portions based on the preset reference point are stored in the storage device of the control unit 11 to set the detailed inspection-requiring portions. The slit light is projected from the second light projection unit 5 toward the detailed inspection-requiring portions, and the unevenness on each of the detailed inspection-requiring portions is measured based on a step on the side edge (the boundary between bright and dark regions) by the slit light. In the case where it is determined in the unevenness determination that the machining scratch or the surface roughness defect exists, the workpiece 2 is treated as a defective product.

Figure 12:
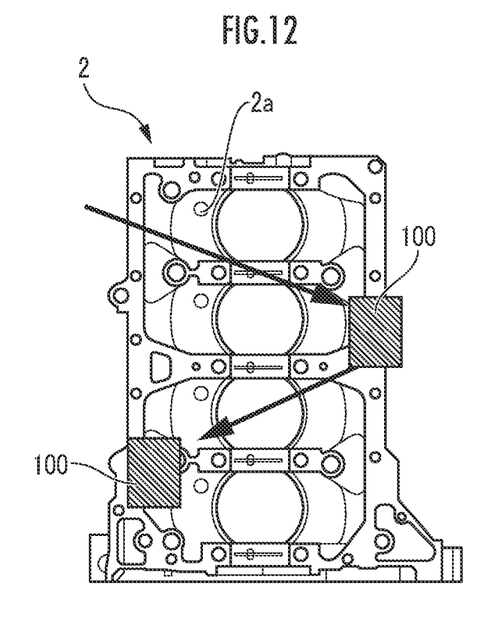
FIG. 12 is an explanatory diagram illustrating the order of image capturing of a detailed inspection in the fifth face (face on the crankshaft side) of the workpiece by arrows, in the workpiece inspection device of the present embodiment.

Next, the cylinder block serving as the workpiece 2 is placed on the table 3 in the state where the face 2a (a face of FIG. 10) on a crankshaft side faces upward so that the first face 2c and the third face 2d of the cylinder block are held. As illustrated in FIGS. 9 to 12, the images are captured in order of a fourth face 2e, a fifth face 2a, and a sixth face 2f. When the detailed inspection-requiring portions are set, the three-dimensional inspection for determining the height difference is performed as illustrated in FIG. 12 (FIG. 12 illustrates the fifth face 2a as one face).

According to the workpiece inspection device 1 and the workpiece inspection method of the present embodiment, an image of only a portion that is determined to require a detailed inspection when an image is captured using the first light projection unit 4 is captured using the second light projection unit 5, and the quality determination unit 10 of the control unit 11 determines the quality of the cylinder block serving as a final workpiece 2. Accordingly, there can be provided the workpiece inspection device 1 that is capable of performing an inspection with high accuracy and reducing a cycle time of the inspection.

According to the present embodiment, even when images of the inspection target face of the workpiece 2 formed by the first light projection unit 4 and the second light projection unit 5 that project the light at different incidence angles, respectively, are captured by a single image capturing unit 6, it is possible to adjust the focus of the image capturing unit by adjusting the relative distance between the table 3 and the image capturing unit fixing part 7 using the linear movement mechanism 8.

In the present embodiment, the table 3 is provided with the moving mechanism 12 configured to move the workpiece 2, and the image capturing unit fixing part 7 is disposed at an interval from the table 3 to reduce or prevent the transmission of vibrations from the moving mechanism 12. With such a configuration, the vibrations from the moving mechanism 12 can be less likely to be transmitted to the image capturing unit 6 and the inspection can be performed with high accuracy, even when inspecting the workpiece 2 while moving the workpiece 2 at a relatively high speed using the moving mechanism 12.

Note that the workpiece 2 is not limited to the cylinder block, and may be, for example, a cylinder head, a crankshaft, or a case of a power transmission device.

REFERENCE SIGNS LIST

1 Workpiece inspection device
2 Workpiece
2a One face (face on crankshaft side: fifth face)
2b Other face (gasket face: face on cylinder head side: second face)
2c First face
2d Third face
2e Fourth face
2f Sixth face
3 Table
4 First light projection unit
5 Second light projection unit
6 Image capturing unit
7 Image capturing unit fixing part
8 Linear movement mechanism
9 Turning mechanism
9a Rotation axis
10 Quality determination unit
11 Control unit
12 Moving mechanism
13 Swing mechanism
14 Fixing mechanism
100 Detailed inspection-requiring portion

The invention claimed is:

1. A workpiece inspection device configured to capture an image of a surface of a workpiece by an image capturing unit and determine quality of the workpiece, the workpiece inspection device comprising:
   a table on which the workpiece is placed;
   an image capturing unit fixing part configured to fix the image capturing unit disposed at a position spaced apart from the workpiece;
   a first light projection unit;
   a second light projection unit;
   a linear movement mechanism configured to linearly move the table or the image capturing unit fixing part to freely adjust a relative distance between the table and the image capturing unit fixing part;
a turning mechanism that has a rotation axis extending in a direction perpendicular to a moving direction of the linear movement mechanism, configured to freely turn the image capturing unit with respect to the image capturing unit fixing part around the rotation axis;
a quality determination unit configured to determine the quality of the workpiece based on the image captured by the image capturing unit; and
a control unit configured to control the linear movement mechanism and the turning mechanism,
wherein the control unit performs:
a first image capturing step of causing the first light projection unit to project light onto the workpiece and causing the image capturing unit to capture an image;
a detailed inspection portion-determination step of setting a detailed inspection-requiring portion, in a case where there is a portion of the workpiece determined to require a detailed inspection based on the image captured in the first image capturing step;
a second image capturing step of causing the second light projection unit to project light onto the workpiece and causing the image capturing unit to capture an image of the detailed inspection-requiring portion in a case where the detailed inspection-requiring portion is set in the detailed inspection portion-determination step; and
a quality determination step of determining the quality of the detailed inspection-requiring portion based on the image captured in the second image capturing step,
wherein the image capturing unit
is movable by the turning mechanism to a first position where reflection light that is the light projected by the first light projection unit is specularly reflected from the workpiece is received, and
is movable by the turning mechanism to a second position where reflection light that is the light projected at the workpiece by the second light projection unit at an incidence angle which is different from an incidence angle of the light projected at the workpiece by the first light projection unit is specularly reflected from the workpiece is received, and
wherein the linear movement mechanism adjusts a relative distance between the table and the image capturing unit fixing part so that a focus is adjusted to prevent focus deviation caused by a difference due to a difference in the incidence angle between when the reflection light of the light from the first light projection unit is received and when the reflection light of the light from the second light projection unit is received.

2. The workpiece inspection device according to claim 1, wherein
the table is provided with a moving mechanism configured to move the workpiece, and
the image capturing unit fixing part is disposed at an interval from the table to reduce or prevent transmission of vibrations from the moving mechanism.

3. The workpiece inspection device according to claim 2, wherein
the first light projection unit is for measuring a two-dimensional shape,
the second light projection unit is for measuring a three-dimensional shape,
the image capturing unit comprises an image capturing element,
when the two-dimensional shape is measured using the first light projection unit, the detailed inspection-requiring portion is set based on image data detected by the image capturing element, and
when the three-dimensional shape is measured using the second light projection unit, the quality of the workpiece is determined based on image data detected by the image capturing element.

4. The workpiece inspection device according to claim 3, wherein
the workpiece is a cylinder block of an internal combustion engine, and
the table comprises a fixing mechanism configured to fix the cylinder block to the table in a state where the cylinder block is placed on the table with a face of the cylinder block to which a crankcase is to be attached facing the table so that a cylinder arrangement direction of the cylinder block corresponds to a horizontal direction.

5. The workpiece inspection device according to claim 1, wherein
the table is provided with a moving mechanism configured to move the workpiece, and
the image capturing unit fixing part is disposed at an interval from the table to reduce or prevent transmission of vibrations from the moving mechanism.

6. The workpiece inspection device according to claim 1, wherein
the first light projection unit is for measuring a two-dimensional shape,
the second light projection unit is for measuring a three-dimensional shape,
the image capturing unit comprises an image capturing element,
when the two-dimensional shape is measured using the first light projection unit, the detailed inspection-requiring portion is set based on image data detected by the image capturing element, and
when the three-dimensional shape is measured using the second light projection unit, the quality of the workpiece is determined based on image data detected by the image capturing element.

7. The workpiece inspection device according to claim 1, wherein
the workpiece is a cylinder block of an internal combustion engine, and
the table is provided with a fixing mechanism configured to fix the cylinder block to the table in a state where the cylinder block is placed on the table with a face of the cylinder block to which a crankcase is to be attached facing the table so that a cylinder arrangement direction of the cylinder block corresponds to a horizontal direction.

8. A workpiece inspection method, comprising:
a first image capturing step of moving an image capturing unit using a turning mechanism to a first position and projecting light onto a workpiece by a first light projection unit and capturing an image of the workpiece by an image capturing unit, the first position being a position where reflection light that is the light projected by the first light projection unit is specularly reflected from the workpiece is received;
a detailed inspection portion-determination step of setting a detailed inspection-requiring portion, in a case where there is a portion of the workpiece that is determined to require a detailed inspection based on the image captured in the first image capturing step;

a second image capturing step of moving the image capturing unit using the turning mechanism to a second position and projecting slit light onto the workpiece by a second light projection unit and capturing an image of the detailed inspection-requiring portion by the image capturing unit in a case where the detailed inspection-requiring portion is set in the detailed inspection portion-determination step, the second position being a position where reflection light that is the light projected at the workpiece by the second light projection unit at an incidence angle which is different from an incidence angle of the light projected at the workpiece by the first light projection unit is specularly reflected from the workpiece is received;

a linear adjustment step of using a linear movement mechanism to adjust a relative distance between a table on which the workpiece is placed and an image capturing unit fixing part configured to fix the image capturing unit so that a focus is adjusted to prevent focus deviation caused by a difference due to a difference in the incidence angle between when the reflection light of the light from the first light projection unit is received and when the reflection light of the light from the second light projection unit is received; and a quality determination step of detecting unevenness on a surface of the workpiece from a shape of an edge of the slit light to determine the quality of the detailed inspection-requiring portion based on the image captured in the second image capturing step, wherein the linear movement mechanism is configured to linearly move the table or the image capturing unit fixing part to freely adjust a relative distance between the table and the image capturing unit fixing part, and the turning mechanism has a rotation axis extending in a direction perpendicular to a moving direction of the linear movement mechanism, and is configured to freely turn the image capturing unit with respect to the image capturing unit fixing part around the rotation axis.

* * * * *